(12) United States Patent
Metzger et al.

(10) Patent No.: US 8,273,131 B2
(45) Date of Patent: Sep. 25, 2012

(54) METHOD AND APPARATUS FOR POSITIONING A MULTIPLE PIECE PROSTHESIS

(75) Inventors: Robert Metzger, Wakarusa, IN (US); Duke A Fox, Winona Lake, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 1473 days.

(21) Appl. No.: 11/444,270

(22) Filed: May 31, 2006

(65) Prior Publication Data

US 2007/0288032 A1 Dec. 13, 2007

(51) Int. Cl.
*A61F 2/38* (2006.01)
(52) U.S. Cl. ..................................... 623/20.14
(58) Field of Classification Search ............... 623/16.11, 623/17.15, 20.21, 20.24, 20.25, 20.3, 20.31, 623/20.14
See application file for complete search history.

(56) References Cited

U.S. PATENT DOCUMENTS

| | | | |
|---|---|---|---|
| 4,703,751 A | 11/1987 | Pohl | |
| 4,935,023 A | 6/1990 | Whiteside et al. | |
| 5,234,433 A | 8/1993 | Bert et al. | |
| 5,364,402 A | 11/1994 | Mumme et al. | |
| 5,411,505 A | 5/1995 | Mumme | |
| 5,520,695 A | 5/1996 | Luckman | |
| 5,860,980 A | 1/1999 | Axelson, Jr. et al. | |
| 6,355,067 B1 * | 3/2002 | Bloebaum | 623/16.11 |
| 6,468,280 B1 | 10/2002 | Saenger et al. | |
| 6,482,209 B1 * | 11/2002 | Engh et al. | 606/79 |
| 6,702,821 B2 | 3/2004 | Bonutti | |
| 6,743,258 B1 * | 6/2004 | Keller | 623/20.14 |
| 2004/0249385 A1 | 12/2004 | Faoro | |
| 2004/0249387 A1 | 12/2004 | Faoro | |

* cited by examiner

*Primary Examiner* — Eduardo C Robert
*Assistant Examiner* — Ann Schillinger
(74) *Attorney, Agent, or Firm* — Harness, Dickey (57) ABSTRACT

A method and apparatus for positioning an implant system in anatomy is disclosed. The apparatus can include an alignment member operable to contact an implant portion, a bone, or other appropriate portion. The method can include using the apparatus to assist in positioning a single or multi-piece implant member. Also, a method of aligning a first implant position relative to another implant position is disclosed.

25 Claims, 5 Drawing Sheets

METHOD AND APPARATUS FOR POSITIONING A MULTIPLE PIECE PROSTHESIS

FIELD

A method and apparatus for performing an orthopedic procedure, specifically a method and apparatus for performing an arthroplasty including preparing two portions of a bone.

BACKGROUND

The statements in this section merely provide background information related to the present disclosure and may not constitute prior art.

An anatomy, such as a human anatomy, includes various portions that are operable to move relative to one another. A joint generally allows for two portions, such as bony portions, to move relative to one another. For example, a knee joint is generally formed between the femur and the tibia and also articulation of the femur and the tibia at a selected location. For various reasons, such as disease, age, injury or the like, the various articulating regions may no longer be able to perform the anatomical action of the smooth and pain-free articulation. It may be selected, if possible, to replace the portions of the anatomy with a prosthesis. Prostheses, such as those generally known in the art, vary widely in their construction, method of implantation, and the like.

Generally, a total knee arthroplasty (TKA) requires a replacement of the entire articulation or condylar portion of the femur and the entire articulation region of the tibia. Generally, a single element replaces each of the articulating portions of the femur. Nevertheless, it may be desirable to replace only selected portions of the femur, such as the medial and lateral condyles that articulate with the tibia. It may be desirable to maintain the remaining portions of the femur for various purposes, such as bone retention, cartilage retention, or the like. Therefore, it may be desirable to provide a method and apparatus for positioning and implanting a plurality of articulating elements to articulate with a selected portion of the anatomy.

It can also be desirable to provide an implant system that allows for performing more than a single cut or resection on a selected bone based upon or aligned relative to a first cut or resection on a bone. The system may allow for positioning a substantially single piece implant relative to the cut bone surface once the one or more cuts are made. Therefore, a system that allows for forming multiple cuts on a single bone aligned relative to a first cut may be desirable.

SUMMARY

A method and apparatus for positioning and implanting a prosthesis relative to a joint is disclosed. The apparatus can be any appropriate apparatus that can allow for aligning a first portion of the anatomy with a second portion of the anatomy to allow for positioning the prosthesis relative to the anatomy. Generally, the various portions of the anatomy can be aligned for resection, such as aligning a first resected portion relative to a second resected portion to achieve a result. Alternatively, a first implant member can be aligned relative to a second implant member to achieve a selected result. This can allow various implant members to not be interconnected in a fixed manner, either during or after the implantation procedure. An implant, however, can be formed as a single piece.

According to various embodiments a system for positioning a prosthesis is disclosed. The system can include a first alignment portion and a second alignment portion. An adjustment mechanism can be provided to interconnect with at least one of the first alignment portion, the second alignment portion, or combinations thereof. Also, a manipulation member can extend from at least one of the first alignment portion, the second alignment portion, or combinations thereof. At least one of the first alignment portion or the second alignment portion is adjustable relative to the other of the first alignment portion or the second alignment portion to assist in determining a position of the first alignment portion to the second alignment portion.

According to various embodiments a method of positioning a prosthesis member on a single bone in a joint of an anatomy is disclosed. The method can include obtaining access to the joint. A first prosthesis member can be positioned on a first portion of the single bone and a position of a resection on a second portion of the single bone can be determined or obtained. The resection on the second portion of the single bone and a second prosthesis member can be positioned on the single bone.

According to various embodiments a method of positioning a prosthesis member on a single bone in a joint in an anatomy is disclosed. The method can include obtaining access to the joint and performing a first resection on a first portion of the single bone at a first location. A position of a second resection on a second portion of the single bone can be obtained or determined and a second resection based upon the obtained position can be performed. A single piece prosthesis member or a multiple piece prosthesis assembly can be installed on the single bone.

According to various embodiments a method of positioning a prosthesis member on a single bone in a joint in an anatomy is disclosed. The method can include obtaining access to the joint and performing a first resection on a first portion of the single bone. A first prosthesis member can be positioned relative to the single bone near the first portion. A position of a second resection on a second portion of the single bone can be determined based at least in part on a position of the first prosthesis member after it is positioned and the second resection can be formed on the single bone.

Further areas of applicability will become apparent from the description provided herein. It should be understood that the description and various examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION OF VARIOUS EMBODIMENTS

The following description is merely exemplary in nature and is not intended to limit the present disclosure, application, or uses.

Figure 1:
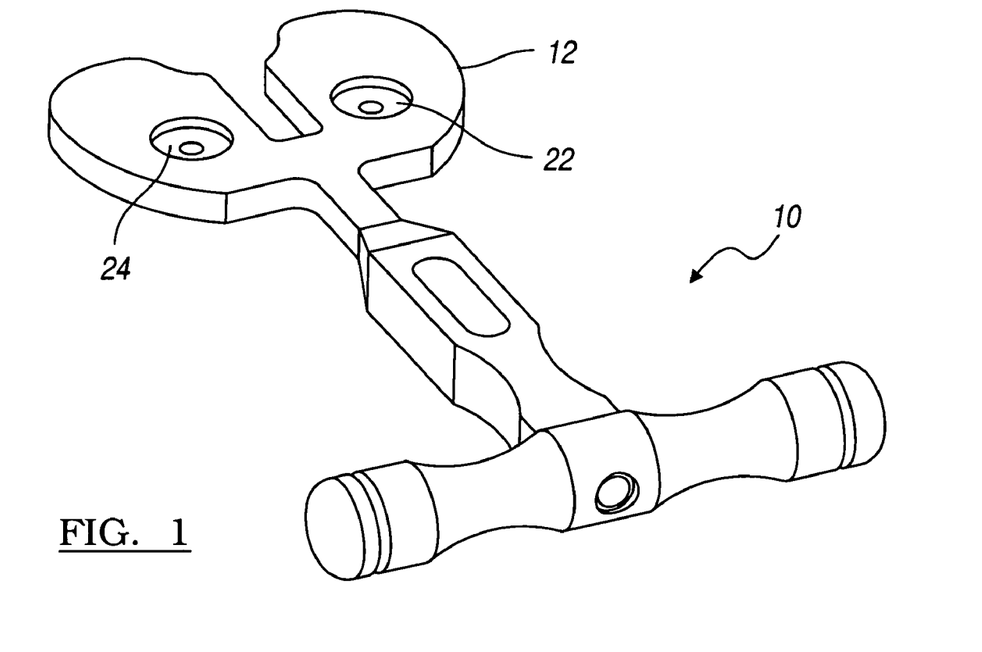
FIG. 1 is a perspective view of an alignment device according to various embodiments.
Figure 2:
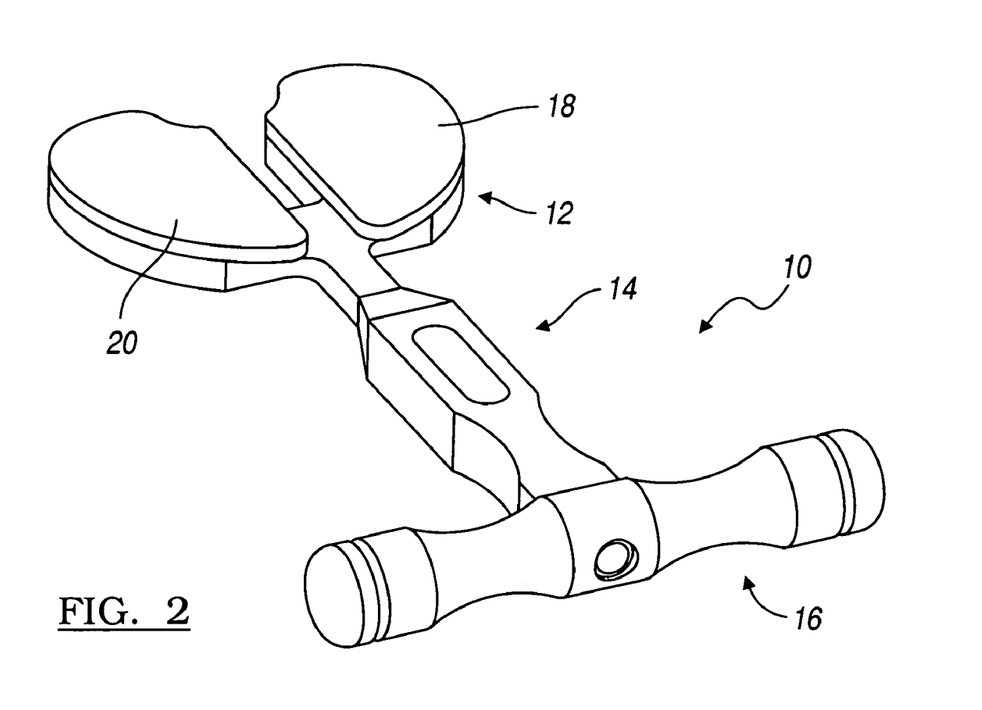
FIG. 2 is a perspective view of an assembled alignment device according to various embodiments.

With reference to FIGS. 1 and 2, an alignment or spacing instrument 10 is illustrated. The spacing instrument 10 can include a spacer portion 12 that extends from an end of a rod 14 that can be interconnected with a handle 16. Operable with the spacer portion 12, can be an adjustment mechanism, the adjustment mechanism can include various modular spacers, such as a modular spacer 18 and a modular spacer 20. The modular spacers 18, 20 can be interconnected or operable with the spacer portion 12 to achieve a selected spacing alignment.

The modular spacers can be provided in any appropriate number and size. For example, a plurality of spacers can include dimensions, such as a height dimension, that varies by about 2 mm a piece. The various spacers can be positioned in the connection ports 22, 24 of the spacer portion 12. In this way, the spacer instrument 10 can be used to align or select an alignment of the one bone relative to a second bone. For example, the spacer instrument 10 can be used to align a femur relative to a tibia.

In preparing a selected joint for placement of a prosthesis, it is generally desirable to maintain or re-obtain a substantially natural or selected articulation and alignment of the bones. The selected alignment can be obtained by positioning an instrument to contact a first portion of the bone to achieve or assist in a resection or cutting a second portion of the bone relative to the first portion. As discussed herein, an alignment tool can be positioned on the bone itself, relative to an implant member, relative to a first cut portion of the bone, or the like, to assist in or to achieve a resection of a selected second portion of the bone. It will be understood that the prostheses that are positioned relative to the resected bone can be a multi-component prosthesis, a multi-piece prosthesis, or a single piece prosthesis.

A multi-component prosthesis can include a prosthesis that includes two prosthetic members that are not integrally interconnected, such as two separate unicondylar implants. A multi-piece implant can include an implant member that includes more than one piece that is integrally interconnected at some point. Finally, a single piece implant can include an implant that is substantially formed as a single piece and implanted relative to the selected joint as a single piece.

Although an exemplary alignment instrument 10 is illustrated, any appropriate alignment instrument can be provided to align various portions of a prosthesis or joint. It will be understood that the alignment instrument 10 is merely exemplary of any appropriate instrument that can be used to achieve an appropriate alignment. Such other alignment instruments can be reasonably understood by one skilled in the art to achieve a selected result.

A selected method of achieving a result will now be discussed in relation to FIGS. 3-7. The method can allow aligning a selected implant relative to another one. Therefore, two implants, or any appropriate number of implants, can be aligned relative to one another to achieve a selected result in the anatomy. As discussed above, however, an alignment instrument according to various embodiments can be used to align joint portions or bone portions for positioning a single piece implant.

Figure 3:
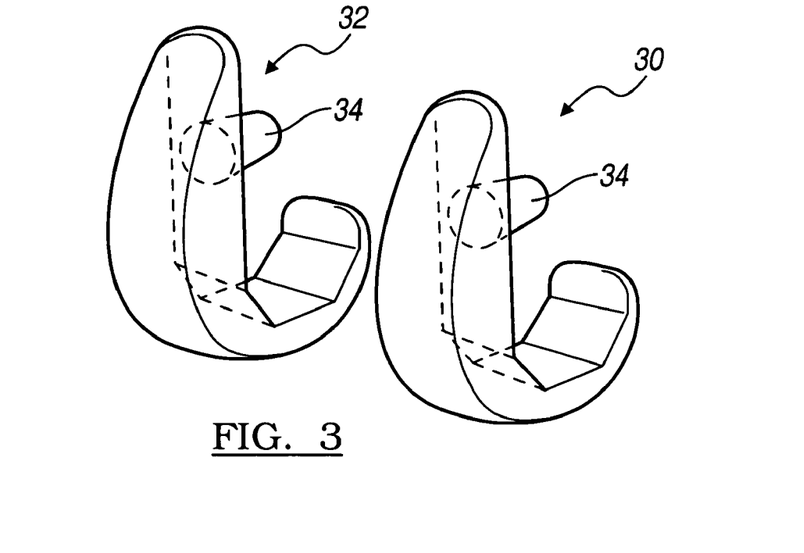
FIG. 3 is a perspective view of an implant system according to various embodiments.

With reference to FIG. 3, a first unicondylar prosthesis 30 can be provided and a second unicondylar prosthesis 32 can also be provided. The various unicondylar prostheses 30, 32 can be provided to replace a selected portion of the anatomy, such as a medial femoral condyle and a lateral femoral condyle. It will be understood that the unicondylar implants 30, 32 can be any appropriate members, such as the Oxford® Unicompartmental Knee Replacement™ sold by Biomet, Inc., of Warsaw, Ind., USA. The unicondylar implants 30, 32 can include various features, such as a peg 34 that is operable to extend into a selected bore formed in the bone. Further, other fixation mechanisms can be used to fix the unicondylar implants 30, 32 to a selected portion of the anatomy. The unicondylar implants 30, 32 are generally provided to replace a selected condyle of the femur in an anatomy; although it can be selected to provide implants to replace both articulating condyles of the femur.

Figure 4:
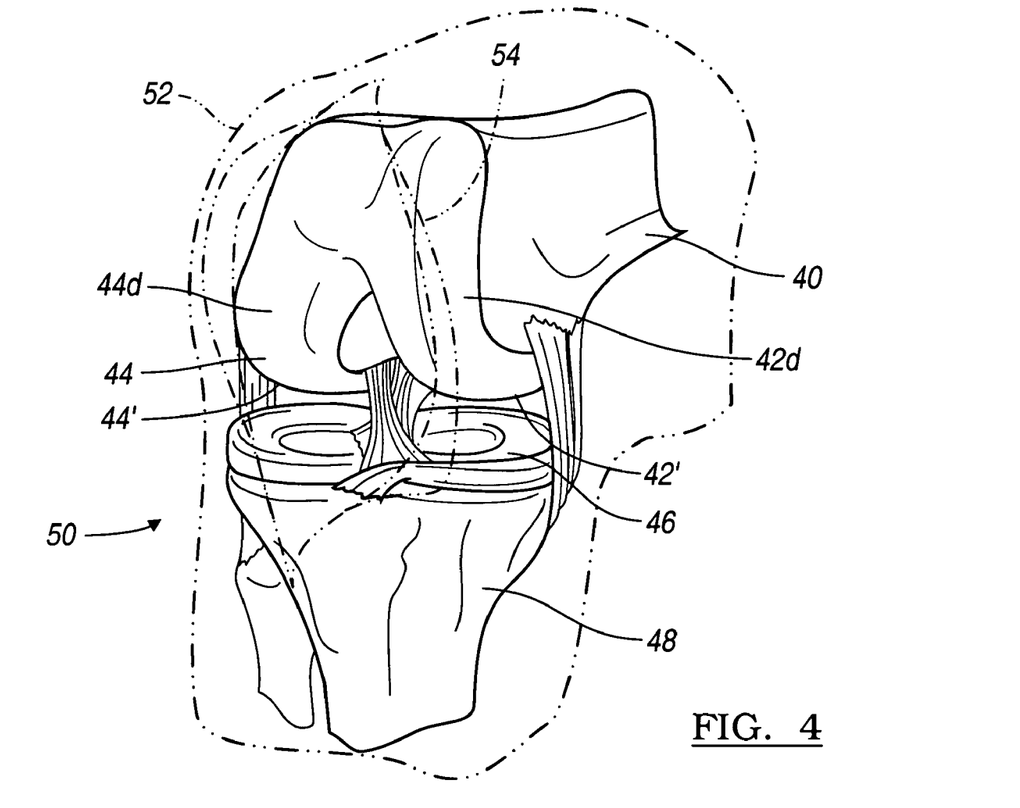
FIG. 4 is a perspective view of a portion of an anatomy.

With reference to FIG. 4, a femur 40 generally includes a first condyle, which can be a medial or lateral condyle, but is illustrated as a medial condyle 42 and a second condyle 44, which can also be a medial or lateral condyle, but is illustrated as a lateral condyle. The condyles 42, 44 can articulate with a tibial surface or plateau 46 that extends from the tibia 48. It will be understood by those skilled in the art that generally soft tissues portions are formed on the tibial plateau 46 and can also be formed on the condyles 42, 44. Nevertheless, generally when the implants 30, 32 are to be positioned in a joint, such as a knee joint 50, at least parts of the soft tissue portions may be worn away or need replacement. The condyles 42, 44 may need to be replaced so that the implants 30, 32 can replace the femoral condyles. Although the femoral condyles are replaced, the tibial plateau 46 and the soft tissue associated therewith can remain substantially intact and can be formed or maintained to articulate with the implants 30, 32. Therefore, the implants 30, 32 can be implanted to replace the articulating portions of the condyles 42, 44 as discussed herein.

Soft tissue 52, such as skin, muscle, adipose tissue, and the like generally surrounds the knee joint 50. To obtain access to the condyles 42, 44 of the femur 40, an incision 54 is generally made in the soft tissue 52. Incision 54 can be any appropriate size to achieve access to the condyles 42, 44. For example, the incision 54 can be about 1 cm to about 20 cm, such as about 13-20 cm, in length. Nevertheless, it will be understood that the incision 54 can be selected by a user to achieve a selected result.

Once the incision 54 has been formed in the soft tissue 52, access can be obtained to the condyles 42, 44 to prepare them for implantation of the implants 30, 32. It will be understood that any appropriate mechanism and instruments can be used to prepare the condyles 42, 44 to implant the prostheses 30, 32. For example, as mentioned above, the Oxford® Unicompartmental Knee Replacement™ system can be used to prepare the condyles 42, 44 for implantation of the implants 30, 32. Generally, the preparation can include resecting various portions of the condyles 42, 44, milling portions of the condyles 42, 44, or any other appropriate mechanisms or methods. An inferior portion of the condyles, such as portions 421 and 441 can be contacted with a saw guide to remove an inferior portion of the condyles 42, 44. Further, various resection or milling instruments can be used to resect or remove portions of the distal portions of the condyles, such as the distal portion 42d and 44d.

Figure 5:
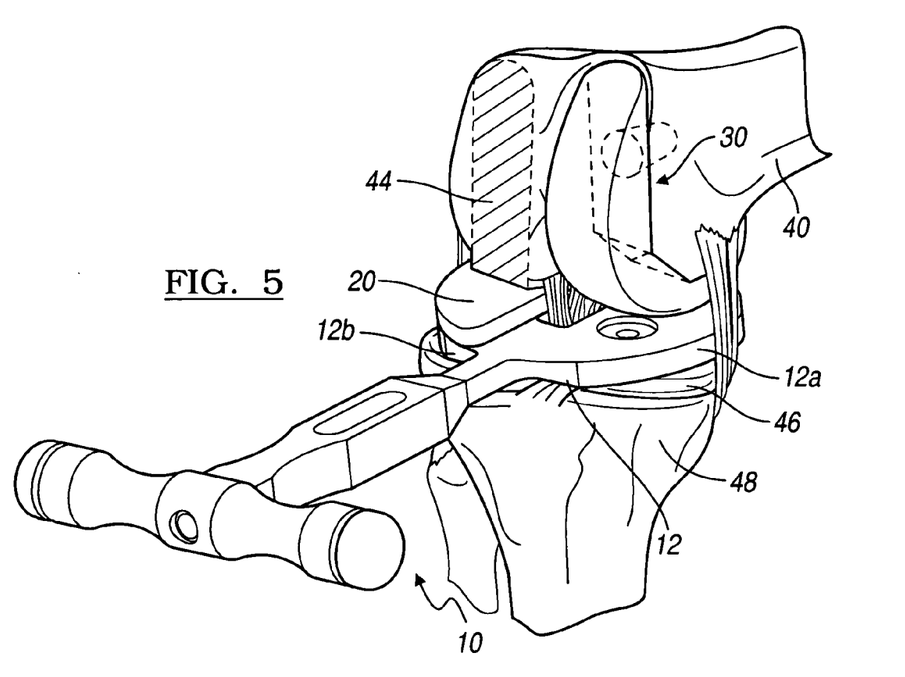
FIG. 5 is a perspective view of an environmental view of an alignment device in use according to various embodiments.

Once the various resections on the femur 40 are made, a selected one of the implants, such as the first prosthesis member 30, can be positioned relative to the femur 40 in any appropriate manner. For example, various cements (e.g., polymethylmethacrylate) can be used to assist in fixing the prosthesis 30 to the femur 40. Also, various other mechanical fixation mechanisms can be used to fix the implant 30 relative to the femur 40. The fixation mechanisms can be selected based upon user preference, the strength of the anatomy, or any other appropriate reason. Nevertheless, once the implant 30 is positioned relative to the femur, the alignment tool 10 can be used to insure an appropriate positioning of the second implant member 32.

For example, the alignment tray 12 can be positioned between the tibial plateau 46 and the first implant portion 30. A first side of the alignment tray 12a can be formed to touch both the tibial plateau 46 and the implant portion 30. The second half of the alignment tray 12b can be positioned to touch the tibial plateau 46 and either touch the resected second condyle 44 or the augment or modular member 20 can be selected to achieve contact between the femoral condyle 44 and the tibial plateau 46. It can be understood that the alignment tool 10 can be used to insure an appropriate alignment between the tibia 48 and the femur 40. Although it is illustrated that the alignment tool 10 is used while the knee joint is in flexion, it will also be understood that alignment can be achieved during extension of the joint.

The alignment tool 10 can be positioned between the tibial plateau 46 and the implant portion 30 and between the tibial plateau 46 and the resected condyle 44, to assist in obtaining the selected location, such as the second location. The alignment tool 10 can be used to insure an appropriate alignment of the femur 40 relative to the tibia 48 and also insure an appropriate gap between the femur 40 and the tibia 48. For example, as is understood in the art, various soft tissue releases or tensionings may be necessary to insure an appropriate alignment of the femur 40 with the tibia 48. Therefore, the alignment tool 10 can be used to insure appropriate alignment of the femur 40 relative to the tibia 48 while the implant member 30 is in place and the second condyle 44 is in a resected and prepared condition.

Figure 6:
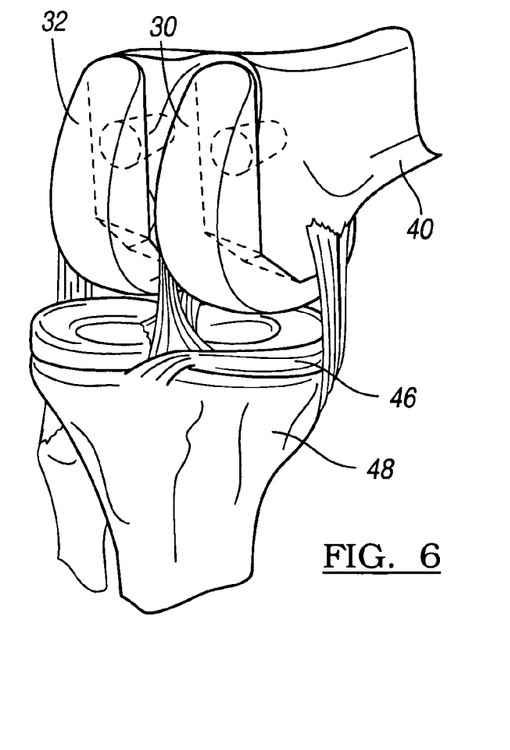
FIG. 6 is an environmental implanted view of a system of implants according to various embodiments.

Once the appropriate alignment of the first implant 30 is configured relative to the second condyle 44, the second implant portion 32 can be implanted to complete the procedure. Therefore, the two implant members 30, 32 can be implanted relative to the femur 40, one based upon the position of the other. This can help assure appropriate alignment of the femur 40 relative to the tibia 48 and also of the second implant member 32 to the first implant member 30.

It will be understood that aligning portions of the anatomy to achieve an appropriate interaction with multiple implant members relative to the anatomy can also be performed. For example, with reference to FIG. 7, the alignment tool 10 can be positioned relative to the femur 40, which has the first condyle 42 resected in an appropriate manner. The first part 12a of the alignment tray 12 can be positioned relative to the second condyle 42 to assist in achieving a selected resection of the second condyle 44. The appropriate modular member 20 can be interconnected with the alignment tray 12 to allow for alignment of a resection block 60 on the second condyle 44. The resection block 60 can be interconnected with the femur 40 in any appropriate manner, such as with two connecting pins 62 and 64. Once the resection block 60 has been interconnected with the femur 40, the alignment tool 10 can be disengaged from the femur 40. Once the alignment tool 10 is removed, the resection block 60 can be maintained in place to guide a resection of the inferior portion of the femur 44l. In this manner, the inferior resection of the femur 40, for both the first condyle 42 and the second condyle 44, can be substantially aligned with the alignment tool 10. This can allow the two implant members 30, 32 to be positioned on the femur 40 in a substantially aligned manner to achieve a selected result. It will be understood that the alignment tool 10 can be used to align any appropriate resection of the femur 40 and using it to align the inferior resection is merely exemplary.

Figure 7:
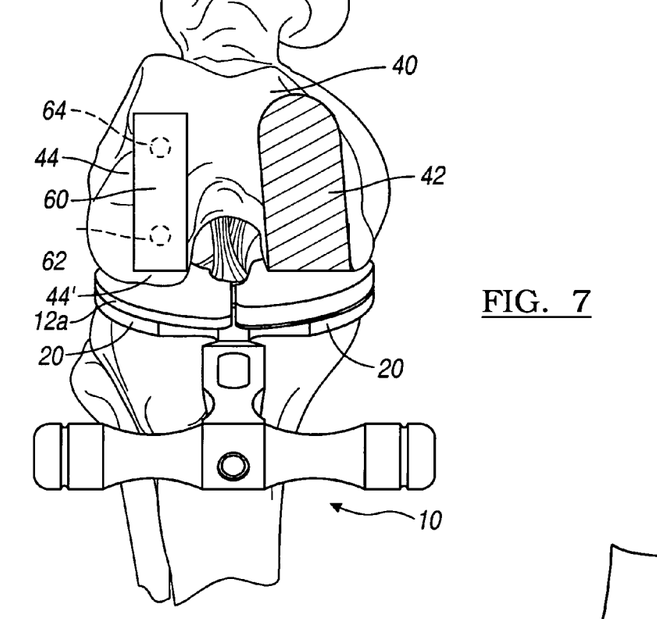
FIG. 7 is a perspective view of an environmental view of an alignment device in use according to various embodiments.

Although the inferior resections can be selected to be matched or aligned with the alignment tool 10, between the first condyle 42 and the second condyle 44, the distal resection of the condyles 42, 44 can also be substantially matched to one another with the alignment tool 10 or any appropriate alignment tool.

Figure 8:
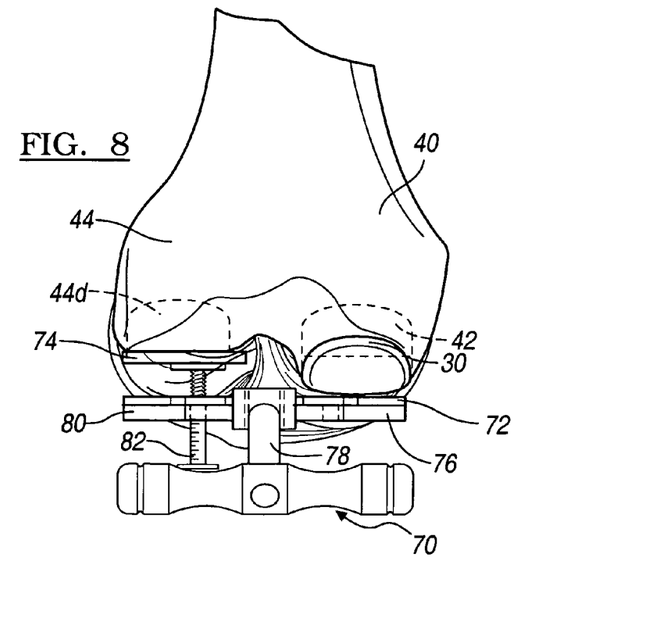
FIG. 8 is a perspective view of an environmental view of an alignment device in use according to various embodiments.

It will be understood that although the alignment tool 10 has been exemplary described with modular portions, that can be removed, to allow for achievement of a selected alignment the alignment tool 10 can be used with adjustable portions to achieve similar results. For example, with reference to FIG. 8, once the first condyle 42 of the femur 40 is prepared and the first implant member 30 is positioned relative thereto, an alignment tool 70 can be used to insure an appropriate resection of the second condyle 44. The alignment tool 70 can be used to align any appropriate resection such as the resection of the distal portion 44d thereof. The alignment tool 70 can include a first foot or contact member 72 and an adjustable or second contact foot 74. The two feet 72, 74 can be interconnected with a connection member 76 that can also extend from a handle 78 for manipulation by a user. An adjustment mechanism 80 can be provided relative to the second foot 74 to move the second foot 74 relative to the alignment tool 70, such as relative to the first foot 72. Any appropriate indication, such as markings 82 on the adjustment portion 80, can be used to indicate a difference between the first foot 72 and the second foot 74. Therefore, one skilled in the art can determine the amount of the second condyle 44 that needs to be resected to achieve an appropriate alignment with the first implant member 30 once the two members are implanted relative to one another.

Figure 9:
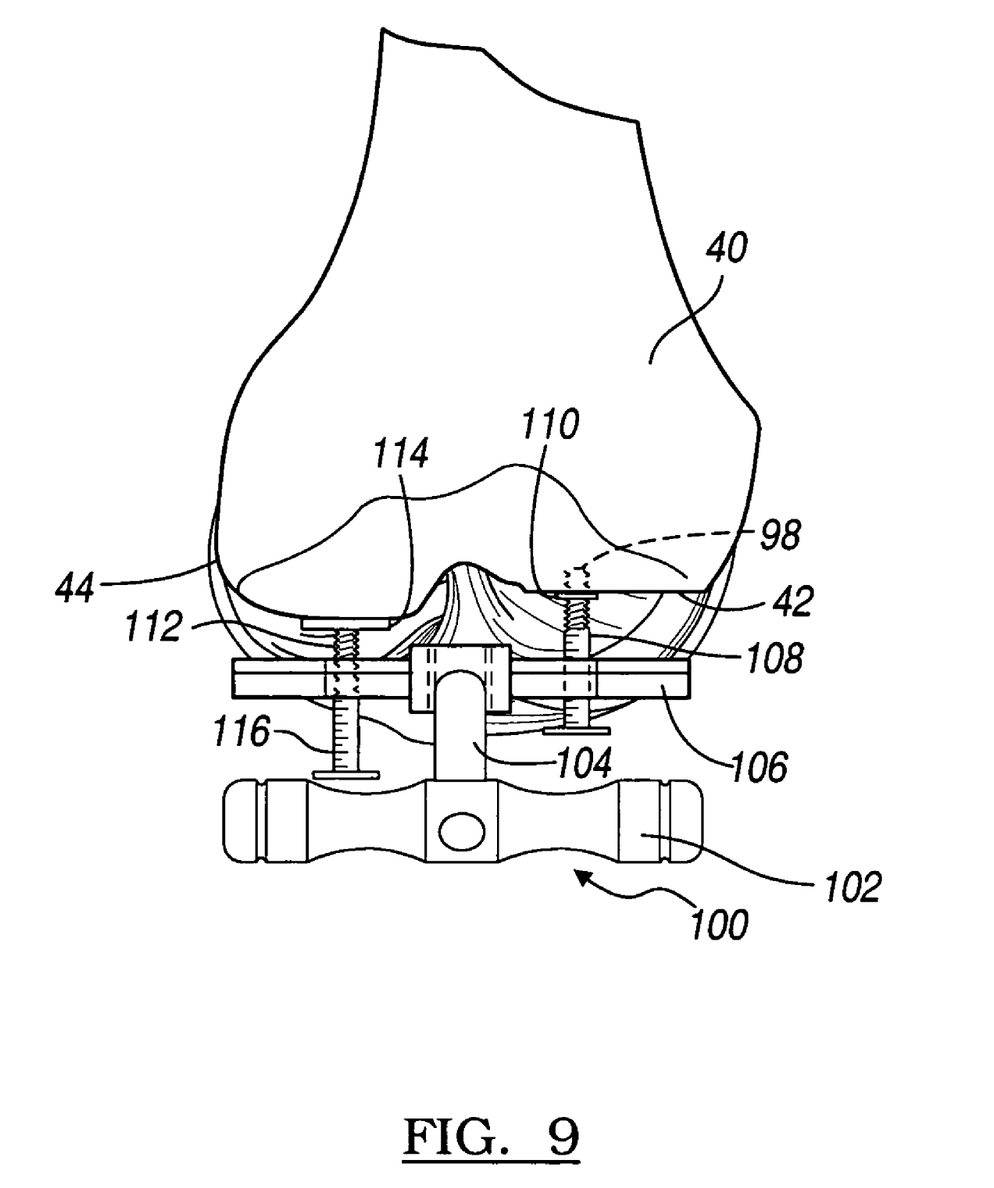
FIG. 9 is a plan environmental view of a guide assembly according to various embodiments.

Although the alignment tool 10, or an alignment tool according to various embodiments, can be used to align a second resection relative to a first positioned implant member, it will be understood that a second resection can be aligned in the appropriate portion. For example, a first and second resection can be aligned relative to one another on a single bone, such as a femur, including an inferior or a distal resection of a femur. With reference to FIG. 9, an instrument can be positioned relative to a first portion of the bone, such as the femur. The femur 40 can be resected with a selected instrument, such as a mill. The mill can be any appropriate mill such as the mill provided with the Oxford® Unicompartmental Knee Replacement™ from Biomet, Inc. of Warsaw, Ind. The mill can be used to resect a selected portion, such as a distal portion of the femur 42. The mill can be used to mill the distal portion of the femur 42 in any appropriate manner, but may be interconnected with a spigot member that is positioned within a bore 98 formed in the distal end of the femur 42.

An alignment tool 100 can be interconnected with the bore 98 formed in the distal portion of the femur 42. A manipulation portion can include a hand graspable portion 102 and a rod 104 interconnected with an alignment bar or section 106. An adjustment mechanism can include a first threaded member 108 that can interconnect with the bore 98 formed in the distal portion of the femur 42. The first adjustment mechanism 108 can include a stop member 110 so that it is only moved a certain distance into the bore 98. The adjustment mechanism 108 can be interconnected with the alignment bar 106 to position a second adjustment member 112 relative to the second distal condyle 44.

The second adjustment member 112 can include portions similar to the adjustment mechanism 74, discussed above. A plate or member 114 can engage or touch a portion of the condyle 44 and a demarcation or marking 116 can be reviewed relative to the alignment member 106 to determine a position of the condyle 44 relative to the resected distal condyle 42. This can be used to determine a resection amount, position of a resection guide, or any appropriate action. In this way, the second condyle 44 can be resected relative to the first condyle 42 in an appropriate manner. It will be understood that the resection can be any appropriate resection, such as one with a saw, one with a mill, or the like. Nevertheless, the second resection can be aligned relative to the first resection to achieve and alignment of the femur 44. It will be understood, however, that any appropriate member or bony member can be resected with the described apparati according to various embodiments. This can allow for positioning of any appropriate prosthesis such as a multi-piece prosthesis, and multi-piece integral prosthesis, or a single piece prosthesis.

Nevertheless, the tools used to resect the femur 40 can be moved relative to the femur 40 so that a single cut need not resect each portion in a selected plane of the femur 40 to achieve an aligned resection. It is understood the first condyle 42 can be resected at a different time than the second condyle 44 with the alignment tool 100. It will be understood that any appropriate single piece implant can be provided to interconnect with the resected portion of the femur 40 using the alignment instrument 100, such as the AGC®, Maxim®, or Asent™ knee systems provided by Biomet, Inc. of Warsaw, Ind. Exemplary multiple piece integral prostheses include those disclosed in currently pending and commonly assigned U.S. patent application Ser. No. 10/901,475 filed Jul. 28, 2004, incorporated herein by reference.

Therefore, it will be understood that various methods can be used to achieve an appropriate alignment of two different members in a single joint. For example, the second condyle implant 32 can be aligned relative to the first condyle implant 30, both distally and inferiorly, or medially or laterally, or any other appropriate manner. Further, resection of the second condyle 44 relative to the first condyle 42 can also be used as an alignment mechanism. Therefore, one skilled in the art will understand that a multi-component implant, such as two unicondylar implants, can be aligned one relative to the other to achieve an appropriate alignment after implantation. Although, one skilled in the art may understand that a single unicondylar implant can be aligned relative in a joint space, being able to three dimensionally align one implant relative to another to achieve a substantially aligned result for a generally anatomical alignment and positioning of two implant portions in a single joint, such as a medial/lateral portion, can now be achieved.

What is claimed is:

1. A method of positioning a prosthesis member on a single bone in a joint of an anatomy, comprising:
   obtaining access to the joint;
   positioning a first prosthesis member at a first location on a first portion the single bone;
   obtaining a second location of a resection on a second portion of the single bone different from the first portion after positioning the first prosthesis member at the first location on the first portion the single bone, including:
      contacting the positioned first prosthesis member on the first portion of the single bone with an alignment instrument; and
      moving a portion of the alignment instrument relative to the second portion of the single bone;
   wherein the alignment instrument to contact the first prosthesis member is separate and different from a resection instrument for performing the resection;
   performing a resection at the obtained second location on the second portion of the single bone with the resection instrument; and
   positioning a second prosthesis member at the second location on the single bone.

2. The method of to claim 1, wherein obtaining access to the joint includes forming an incision in soft tissue surrounding the joint.

3. The method of claim 1, wherein positioning a first prosthesis member on the first portion of the single bone includes positioning a unicondylar implant relative to a single condyle on a femur.

4. The method of claim 1, wherein obtaining the second location of a resection of a second portion of the single bone further comprises:
   contacting a spacer portion of the alignment instrument with the positioned first prosthesis member at the first location on the single bone; and
   positioning a resection guide relative to the second portion of the single bone.

5. The method of claim 4, wherein performing the resection of the second portion of the single bone includes resecting the second portion of the single bone with the resection instrument being guided by at least a portion of the resection guide.

6. A method of positioning a prosthesis member on a single bone in a joint in an anatomy, comprising:
   obtaining access to the joint;
   performing a first resection on a first portion of the single bone at a first location with a first instrument;
   obtaining a second location of a second resection on a second portion of the single bone by contacting at least the first portion with a second instrument after performing the first resection;
   performing the second resection based upon the obtained second location with the first instrument or a third instrument; and
   implanting a prosthesis member relative to at least one of the first location, the second location, or combinations thereof on the single bone;
   wherein the second instrument is different and separate from the first instrument and the second instrument.

7. The method of claim 6, wherein performing the first resection of the first portion of the bone with the first instrument includes sawing the first portion of the bone, milling the first portion of the bone, or combinations thereof.

8. The method of claim 6, wherein obtaining the second location of the second resection on a second portion of a single bone includes:
   contacting the resected first portion of the single bone with the second instrument that is different from the first instrument;
   moving a second portion of the second instrument relative to the second portion of the single bone including at least one of positioning a modular member relative to the second portion of the second instrument to determine a position for the second resection or adjusting a second portion of the second instrument to determine a position for the second resection; and
   determining the second location of the second resection based upon the position of the second portion of the second instrument.

9. The method of claim 6 further comprising:
determining an alignment of the single bone relative to a second bone;
wherein obtaining a position of a second resection on a second portion of a single bone includes determining the alignment of the single bone relative to the second bone.

10. The method of claim 6, wherein the single bone includes a femur and the first portion of the single bone includes a condyle of the femur.

11. The method of claim 10, wherein obtaining the second location of the second resection on a second portion of a single bone comprises:
implanting a first portion of the prosthesis member at the first location;
contacting the implanted first portion of the prosthesis member with the second instrument that is different from the first instrument; and
determining the second location relative to the first portion of the implanted prosthesis member with the second instrument.

12. The method of claim 6, wherein implanting a prosthesis includes implanting a single piece prosthesis, a multiple piece integral prosthesis, a multiple piece prosthesis or configurations thereof.

13. A method of positioning a prosthesis member on a single bone in a joint in an anatomy, comprising:
obtaining access to the joint;
performing a first resection on a first portion of the single bone at a first location;
implanting a first prosthesis member relative to the single bone near the first location at a final location, wherein the implanted first prosthesis member is operable to replace a portion of the single bone;
obtaining a second location of a second resection on a second portion of the single bone based at least on directly contacting an alignment instrument onto the first prosthesis member after the first prosthesis member is implanted at the final location on the single bone and moving a second portion of the instrument relative to the second portion of the single bone;
determining an amount of resection of the second portion of the single bone based upon the implanted final position of the first prosthesis member and the moved second portion of the instrument; and
forming the second resection on the single bone based on the determined amount of the second resection.

14. The method of claim 13, further comprising:
positioning a resection guide relative to the second portion of the single bone based upon a position of the second portion of the instrument.

15. The method of claim 14, wherein positioning a resection guide includes positioning a saw guide, positioning a milling guide, positioning an ablator, or combinations thereof.

16. The method of claim 13, wherein obtaining a second location of the second resection includes obtaining a distal resection position, obtaining an inferior resection position, obtaining a superior resection position, or combinations thereof.

17. The method of claim 13, further comprising:
implanting a second prosthesis member onto the single bone near the second location.

18. The method of claim 17, further comprising:
replacing a first condyle of a femur with the first prosthesis member and replacing a second condyle of the femur with the second prosthesis member.

19. The method of claim 13, wherein performing a first resection or performing a second resection includes milling the single bone.

20. The method of claim 19, wherein milling the single bone includes milling the first resection and the second resection from a single guide position.

21. A method of positioning a prosthesis member on a single bone in a joint in an anatomy, comprising:
obtaining access to the joint including a knee joint;
performing a first resection on a first portion of the single bone at a first location to resect a first condyle of a femur;
implanting a first prosthesis member relative to the single bone near the first location at a final location, wherein the implanted first prosthesis member is to replace a portion of the resected first condyle;
obtaining a second location of a second resection on a second portion of the single bone to resect a second condyle of the femur based at least on:
directly contacting a first portion of an alignment instrument onto a surface of the first prosthesis member after the first prosthesis member is implanted at the final location on the single bone, and
moving a second portion of the alignment instrument relative to the second portion of the single bone to determine an amount of resection of the second portion of the single bone based upon the determined final position of the first prosthesis member;
positioning a resection guide relative to the second condyle of the femur based on the moved second portion of the alignment instrument;
removing the alignment instrument after positioning the resection guide;
forming the second resection on the single bone by guiding a resection instrument with the resection guide to resect the second condyle of the femur;
removing the resection guide; and
implanting a second prosthesis member on the second portion of the single bone to replace at least a portion of the resected second condyle of the femur.

22. The method of claim 21, wherein moving a second portion of the alignment instrument includes moving a foot to contact the second condyle of the single bone while the first portion of the alignment instrument is in contact with the implanted first prosthesis member.

23. The method of claim 21, wherein moving a second portion of the alignment instrument includes adding a modular member to the second portion of the alignment instrument to contact the second condyle of the single bone while the first portion of the alignment instrument is in contact with the implanted first prosthesis member.

24. The method of claim 21, wherein positioning a resection guide includes positioning a saw guide, positioning a milling guide, positioning an ablator, or combinations thereof.

25. The method of claim 21, wherein obtaining a second location of a second resection includes obtaining a distal resection position, obtaining an inferior resection position, obtaining a superior resection position, or combinations thereof.

* * * * *

UNITED STATES PATENT AND TRADEMARK OFFICE
CERTIFICATE OF CORRECTION

| | | |
|---|---|---|
| PATENT NO. | : 8,273,131 B2 | Page 1 of 1 |
| APPLICATION NO. | : 11/444270 | |
| DATED | : September 25, 2012 | |
| INVENTOR(S) | : Metzger et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1701 days.

Signed and Sealed this
Twenty-sixth Day of August, 2014

Michelle K. Lee
*Deputy Director of the United States Patent and Trademark Office*